United States Patent [19]
Chow et al.

[11] Patent Number: 5,993,786
[45] Date of Patent: Nov. 30, 1999

[54] ANTI-CARIOUS CHEWING GUMS, CANDIES, GELS, TOOTHPASTES AND DENTIFRICES

[75] Inventors: Laurence C. Chow, Potomac; Shozo Takagi, Gaithersburg; Gerald L. Vogel, Germantown, all of Md.

[73] Assignee: American Dental Association Health Foundation, Gaithersgurg, Md.

[21] Appl. No.: 09/088,869

[22] Filed: Jun. 2, 1998

Related U.S. Application Data

[62] Division of application No. 08/704,420, Aug. 20, 1996, Pat. No. 5,833,954.

[51] Int. Cl.$^6$ ........................................... A61K 7/16
[52] U.S. Cl. .............................. 424/49; 424/439; 424/52
[58] Field of Search ......................... 424/52, 49

[56] References Cited

U.S. PATENT DOCUMENTS

| | | | |
|---|---|---|---|
| 4,765,984 | 8/1988 | Vellekoop et al. | 424/441 |
| 5,348,733 | 9/1994 | Morishima et la. | 424/52 |
| 5,500,206 | 3/1996 | Charbonneau et al. | 424/50 |

*Primary Examiner*—Dwayne C. Jones
*Attorney, Agent, or Firm*—Banner & Witcoff, Ltd.

[57] ABSTRACT

The invention relates to anticarious delivery vehicles, specifically chewing gums, candies, confectioneries, toothpastes, dentifrices and gels. The invention specifically provides chewing gums, candies, confectioneries, toothpastes, dentifrices and gels containing non-toxic sparingly soluble calcium and phosphate compounds as additives, causing the release of calcium and phosphate ions into the oral cavity gradually and persistently for a period no less than 5 minutes. The invention provides released calcium phosphate ions that diffuse into partially demineralized tooth enamel or dentin, leading to remineralization and repair of caries lesions, dental plaque, open dentinal tubules and exposed dentin. The invention thus provides agents and methods for remineralization of teeth and for reducing or eradicating cariogenic challenge in plaque following sucrose intake. The formulations of the invention can thereby produce effective anticaries actions without the use of fluoride. In addition, the formulations of the invention can be used to desensitize hypersensitive teeth.

29 Claims, No Drawings

ANTI-CARIOUS CHEWING GUMS, CANDIES, GELS, TOOTHPASTES AND DENTIFRICES

This application is a divisional application of U.S. Ser. No. 08/704,420, filed Aug. 20, 1996 now U.S. Pat. No. 5,833,954.

This invention was made during research activities that were supported in part by Grants DE05354 and DE10840 from the NIDR to the ADAHF and carried out at the National Institute of Standards and Technology. The Government may have certain rights in the invention.

BACKGROUND OF THE INVENTION

1. Field of the Invention

This invention comprises the use of non-toxic sparingly soluble calcium and phosphate compounds as additives to chewing gums, candies, confectioneries, gels, toothpastes or dentifrices that cause the release of calcium and phosphate ions into the oral cavity gradually and persistently for an appropriate and therapeutically useful period. The released calcium phosphate ions can diffuse into partially demineralized tooth enamel or dentin, leading to remineralization and repair of the caries lesion. The released calcium phosphate ions can also diffuse into dental plaque to cause remineralization of teeth and to reduce or eradicate cariogenic challenge in plaque following sucrose intake. Thus, these formulations can produce effective anticaries actions without the use of fluoride. The released calcium phosphate ions can also cause precipitation of calcium phosphate minerals inside open dentinal tubules and on exposed dentine surfaces to desensitize hypersensitive teeth. These agents will have minimal adverse effects and require little effort on the part of the user.

2. Summary of the Related Art

Chewing gums have the potential of being an effective vehicle for delivering therapeutic agents to teeth because they permit protracted contact of the agent to the teeth with minimal effort on the part of a patient. Despite the recognized desirability of chewing gums as vehicles for delivering anticarious agents to teeth, no effective embodiments of anticarious chewing gums have been developed in the art.

The effectiveness of prior attempts at using potential anticarious agents in chewing gums was reviewed by Edgar and Geddes (1990, *Br. Dent. J.* 24: 173–176). For example, dicalcium phosphate dihydrate (DCPD; $CaHPO_4 \cdot 2H_2O$), was used at a dose of 7.5 wt % and assessed for its effects on the calcium (Ca) and phosphate ($PO_4$) concentrations in saliva (Pickel and Bilotti, 1965, *J. Alabama Med. Soc.* 2: 286–287). A chewing gum containing 10 wt % DCPD was assessed for anticarious effects in two different clinical studies (Finn and Jamison, 1967, *J. Amer. Dent. Assoc.* 74: 987–995; Richardson et al., 1972, *J. Canad. Dent. Assoc.* 6: 213–218). The results from the Richardson study showed that, although sugar-DCPD gum produced a lower caries score than did the gum containing sugar alone, the cariogenicity of the sugar-DCPD gum was equivalent to that of sugar-free gum. The marginal degree of effectiveness of DCPD as an anticaries gum additive in this study was accepted in the art as demonstrating that DCPD was ineffective as an anticarious agent. As a result of this study, there has been little interest or activity in the art in using calcium phosphate-containing gums as anticarious agents.

Recently, the feasibility of using two new calcium phosphate additives in bubble gum has been evaluated for effectiveness in increasing salivary mineral saturation levels and/or enhancing salivation (Chow et al., 1994, *J. Dent. Res.* 73: 26–32). In these in vivo studies, monocalcium phosphate monohydrate (MCPM; $Ca(H_2PO_4)_2 \cdot H_2O$) and an equimolar mixture of dicalcium =phosphate anhydrous (DCPA; $CaHPO_4$) and tetracalcium phosphate (TTCP; $Ca_4(PO_4)_2O$) were used as chewing gum additives. These studies showed that both the MCPM and DCPA/TTCP gums increased the calcium and phosphate concentrations in saliva during a chewing period of 16 minutes. The extent of increase was much greater than those produced by gums containing DCPD. The degree of saturation with respect to tooth mineral was significantly increased by both experimental gums, with the greater increase being produced by the DCPA/TTCP gum.

U.S. Pat. Nos. 5,037,639, 5,268,167, 5,427,768, and 5,437,857, issued to Tung, disclose and claim the use of amorphous calcium phosphate ($Ca_3(PO_4)_2$) and derivatives as chewing gum additives for tooth remineralization. However, evidence that ACP chewing gums actually remineralize teeth was not disclosed.

While some of the above additives have had some efficacy under some conditions, shortcomings have been associated with each. The DCPA/TTCP mixture requires an extensive preparation process: TTCP must be prepared in a furnace at a high temperature (1500° C.) and then blended with commercially-available DCPA after each calcium phosphate salt has been ground to the desired particle size. ACP compounds must be precipitated in aqueous systems, thereby having variable composition and relatively undefined particles size. Also, the stability of ACP in gum base or a gel is likely to be limited, and a stabilizer may be required to achieve the desired shelf life.

Other calcium-containing compounds have been studied for their effectiveness in remineralization of teeth in situ. U.S. Pat. No. 5,378,131 to Greenberg disclosed the use of calcium glycerophosphate as a chewing gum additive for dental health benefits. This patent also disclosed the use of several other calcium compounds, including calcium lactate and calcium gluconate, to achieve an anticaries effect when used as a chewing gum additive. However, chewing gums containing calcium compounds as additives can only raise calcium concentration levels in saliva. In fact, phosphate concentration levels would be expected to be decreased as a result of chewing calcium-containing gums, based on the showing that saliva phosphate levels decrease with increased salivation stimulated by gum chewing (Chow et al., *ibid.*). Thus, these calcium-containing chewing gums disclosed by Greenberg are cariostatic, rather than anticarious. There is thus a need in the art for vehicles that release phosphate ions into the oral cavity in conjunction with increased calcium ion concentration to provide an anticaries effects not found in the gums known in the prior art.

In contrast to the recognized desirability of chewing gum as a vehicle for delivery of anticarious agents, candies have not been generally recognized as a means for delivering calcium and phosphate ions into the oral environment. A major reason for this is that sugar, the major ingredient of candies, is the chief culprit of dental caries. With the advent of sugar-free candies (i.e., candies that do not contain significant amount of fermentable carbohydrates), however, candies can be an effective means of delivering therapeutic agents for dental caries.

SUMMARY OF THE INVENTION

This invention provides chewing gums, sugar-free candies and confectioneries, gels, toothpastes and dentrifrices that are formulated to release calcium and phosphate ions into the mouth of a human patient.

In a first aspect, the invention provides a calcium phosphate-containing composition comprising an acidic chewing gum and further comprises a sparingly-soluble calcium phosphate salt. In a most preferred embodiment, the calcium phosphate salt is α-tricalcium phosphate. In other preferred embodiments, the calcium phosphate salt is dicalcium phosphate anhydrous, dicalcium phosphate dihydrate, octacalcium phosphate or tetracalcium phosphate. Preferably, the sparingly-soluble calcium phosphate salt comprises from about 0.5 to about 10 percent of the gum formulation by weight (weight percent, or wt %). More preferably, the sparingly-soluble calcium phosphate salt comprises from about 1 to about 5 wt % of the gum formulation. In the chewing gums of the invention, the sparingly-soluble calcium phosphate salts are provided with a particle size of less than about 50 μm, and more preferably having a particle size of from about 1 to about 20 μm.

In a second aspect, the invention provides a calcium phosphate-containing chewing gum that comprises a calcium compound and a phosphate salt. In a preferred embodiment, the gum is an acidic gum. In another preferred embodiment, the gum is a neutral gum. In yet other preferred embodiments, the calcium compound is a sparingly-soluble calcium compound. In such embodiments, the sparingly-soluble calcium compound is a calcium salt of glycerophosphate, lactate, gluconate, or fumarate. In other embodiments, the calcium compound is a soluble compound, and is preferably calcium acetate or calcium chloride. In these embodiments, the gum is formulated to slow the release of calcium ions from the soluble calcium compound so that calcium ions are released over a 5 to 15 minute period.

Preferably, the gums provided in this second aspect of the invention are formulated to contain calcium compounds at from about 0.5 to 10 weight percent of the chewing gum. More preferably, the calcium compounds comprise from about 1 to about 5 weight percent of these chewing gums. Additionally, the calcium compounds provided in the gums of this aspect of the invention are provided having a particle size of less than 50 μm, more preferably from about 1 to about 20 μm.

The gums of this aspect of the invention are also formulated to contain a phosphate salt. Preferred phosphate salts include but are not limited to $Na_2HPO_4$, $NaH_2PO_4$, and $Ca(H_2PO_4)_2 \cdot H_2O$. Preferably, the gums in this aspect of the invention are formulated to contain phosphate salts at from about 0.5 to 10 weight percent of the chewing gum. More preferably, the phosphate salts comprise from about 1 to about 5 weight percent of these chewing gums. Additionally, the phosphate salts provided in the gums of this aspect of the invention are provided having a particle size of less than 50 μm, more preferably from about 1 to about 20 μm.

In a third aspect, the invention provides a calcium phosphate-containing composition comprising a candy or confectionery and further comprising a calcium phosphate salt. In preferred embodiments, the candy or confectionery is sugar-free. In a most preferred embodiment, the calcium phosphate salt is α-tricalcium phosphate. In other preferred embodiments, the calcium phosphate salt is β-tricalcium phosphate, monocalcium phosphate monobasic, dicalcium phosphate anhydrous, dicalcium phosphate dihydrate, octacalcium phosphate, tetracalcium phosphate, and mixtures and combinations thereof. Preferably, the calcium phosphate salt comprises from about 0.5 to about 10 percent of the candy formulation by weight (weight percent, or wt %). More preferably, the calcium phosphate salt comprises from about 1 to about 5 wt % of the candy formulation. In the sugar-free candies of the invention, the calcium phosphate salts are provided with a particle size of less than about 50 μm, and more preferably having a particle size of from about 1 to about 20 μm. Sparingly-soluble calcium phosphate salts are appropriate but are not required for this embodiment of the invention, due to the preferred composition of the candies and confectioneries of the invention as described in detail herein. Although sugar-free candies and confectioneries are preferred, calcium phosphate-containing embodiments of the candies and confectionaries of the invention prepared using sugar (specifically, sucrose) are within the scope of the invention. In such embodiments, it will be recognized that the cariostatic and remineralizing benefits of the calcium phosphate components of the inventive candies and confectionaries will outweigh the cariogenic propensity of sugar.

In a fourth aspect, the invention provides a calcium phosphate-containing candy or confectionery that comprises a calcium compound and a phosphate salt. In preferred embodiments, the candy or confectionary is sugar-free. In preferred embodiments, the calcium compound is a sparingly-soluble calcium salt of glycerophosphate, lactate, gluconate, or fumarate. In other preferred embodiments, the calcium compound is a soluble compound, and is preferably calcium acetate or calcium chloride. In these embodiments, the candy is formulated to slow the release of calcium ions from the soluble calcium compound so that calcium ions are released over a 5 to 15 minute period.

Preferably, the candies provided in this aspect of the invention are formulated to contain calcium compounds at from about 0.5 to 10 weight percent of the candy. More preferably, the calcium compounds comprise from about 1 to about 5 weight percent of these candies. Additionally, the calcium compounds provided in the candies of this aspect of the invention are provided having a particle size of less than 50 μm, more preferably from about 1 to about 20 μm.

The candies of this aspect of the invention are also formulated to contain a phosphate salt. Preferred phosphate salts include but are not limited to $Na_2HPO_4$, $NaH_2PO_4$, and $Ca(H_2PO_4)_2 \cdot H_2O$. Preferably, the candies in this aspect of the invention are formulated to contain phosphate salts at from about 0.5 to 10 weight percent. More preferably, the phosphate salts comprise from about 1 to about 5 weight percent of these candies. Additionally, the phosphate salts provided in the candies of this aspect of the invention are provided having a particle size of less than 50 μm, more preferably from about 1 to about 20 μm.

Although sugar-free candies and confectioneries are preferred, calcium phosphate-containing embodiments of the candies and confectioneries of the invention prepared using sugar (specifically, sucrose) are within the scope of this aspect of the invention.

In a fifth aspect the invention provides a calcium phosphate-containing remineralizing gel that comprises a calcium phosphate compound selected from the group consisting of α-tricalcium phosphate, tetracalcium phosphate and monocalcium phosphate monohydrate. Certain of these calcium phosphate-containing embodiments of the invention are provided as a dry mixture of the calcium phosphate compound and, optionally, other components of the gel, to be reconstituted into a gel by the addition of water or other liquid containing advantageous additives (such as flavorings, etc.) immediately before use. In other embodiments of this aspect of the invention are provided a combination of a gel comprising a sparingly-soluble calcium compound and a gel comprising a phosphate salt. In a preferred embodiment, the gel is carboxymethyl cellulose or hydroxypropyl methylcellulose. In another preferred embodiments, the sparingly-soluble calcium compound is a calcium salt of glycerophosphate, lactate, gluconate, or fumarate.

Preferably, the gels provided in this aspect of the invention are formulated to contain sparingly-soluble calcium compounds at from about 0.5 to 10 weight percent of the gel. More preferably, the sparingly-soluble calcium compounds comprise from about 1 to about 5 weight percent of these gels. Additionally, the sparingly-soluble calcium compounds provided in the gels of this aspect of the invention are provided having a particle size of less than 50 µm, more preferably from about 1 to about 20 µm.

Combination gel embodiments of this aspect of the invention are also formulated to contain a gel comprising a phosphate salt. Preferred phosphate salts include but are not limited to $Na_2HPO_4$, $NaH_2PO_4$, and $Ca(H_2PO_4)_2 \cdot H_2O$. Preferably, the remineralizing gels in this aspect of the invention are formulated to contain phosphate salts at from about 0.5 to 10 weight percent of the gel. More preferably, the phosphate salts comprise from about 1 to about 5 weight percent of these gels. Additionally, the phosphate salts provided in the gels of this aspect of the invention are provided having a particle size of less than 50 µm, more preferably from about 1 to about 20 µm.

In preferred embodiments, the gels of the invention are provided wherein each of the calcium-containing and phosphate-containing gels are formulated and kept separate until immediately before use. For use, the gels are mixed and applied to teeth, including the occlusal, proximal, cervical and smooth surfaces of teeth. Remineralization of tooth material as provided by the invention is accomplished by allowing the gels of the invention to remain in contact with the tooth surfaces for a period from about 5 minutes to about 12 hours or overnight. High molecular weight crystal growth inhibitors, including the gelling agents comprising the gels, are also included in the gels of the invention. Fluoride ion can also advantageously be added to such gels.

In a sixth aspect the invention provides a calcium phosphate-containing toothpaste or dentifrice. In preferred embodiments, the toothpastes and dentifrices of this aspect of the invention comprise a calcium phosphate salt selected from the group consisting of α-tricalcium phosphate, tetracalcium phosphate and monocalcium phosphate monohydrate. Certain of these calcium phosphate-containing embodiments of the invention are provided as a dry mixture of the calcium phosphate compound and, optionally, other components of the gel, to be reconstituted into a gel by the addition of water or other liquid containing advantageous additives (such as flavorings, etc.) immediately before use. In additional preferred embodiments, the dentrifrices and toothpastes of the invention comprise a combination of two dentifrice pastes, one dentifrice paste comprising a sparingly-soluble calcium compound and another dentifrice paste comprising a phosphate salt. In addition to the sparingly-soluble calcium and phosphate components of these dentifrices, the inventive dentifrices also comprise active ingredients such as fluoride compounds as well as conventional components of dentifrices. In preferred embodiments, the sparingly-soluble calcium compound is a calcium salt of glycerophosphate, lactate, gluconate, or fumarate.

Preferably, the toothpastes and dentifrices provided in this aspect of the invention are formulated to contain calcium phosphate salts or sparingly-soluble calcium compounds at from about 0.5 to 10 weight percent of the toothpaste or dentifrice. More preferably, the sparingly-soluble calcium compounds comprise from about 1 to about 5 weight percent of these toothpastes and dentifrices. Additionally, the sparingly-soluble calcium compounds provided in the toothpastes and dentifrices of this aspect of the invention are provided having a particle size of less than 50 µm, more preferably from about 1 to about 20 µm.

Embodiments of the toothpastes and dentifrices of this aspect of the invention formulated as combinations are also formulated to contain a toothpaste or dentifrice comprising a phosphate salt. Preferred phosphate salts include but are not limited to $Na_2HPO_4$, $NaH_2PO_4$, and $Ca(H_2PO_4)_2 \cdot H_2O$. Preferably, the toothpastes and dentifrices in this aspect of the invention are formulated to contain phosphate salts at from about 0.5 to 10 weight percent. More preferably, the phosphate salts comprise from about 1 to about 5 weight percent. Additionally, the phosphate salts provided in the toothpastes and dentifrices of this aspect of the invention are provided having a particle size of less than 50 µm, more preferably from about 1 to about 20 µm.

The toothpastes and dentifrices of the invention are provided wherein each of the sparingly-soluble calcium-containing and phosphate-containing dentifrices are formulated and kept separate until immediately before use. For use, the toothpastes and dentifrices are mixed and applied to teeth, including the occlusal, proximal, cervical and smooth surfaces of teeth. Remineralization of tooth material as provided by the invention is accomplished by allowing the toothpastes and dentifrices of the invention to remain in contact with the tooth surfaces for about 1 to about 5 minutes. Fluoride ion can also advantageously be added to such toothpastes and dentifrices. Also advantageously included in the toothpastes and dentifrices of the invention are macromolecular crystal growth inhibitors, preferably cellulose compounds and most preferably carboxymethyl cellulose, or alternatively sodium and potassium pyrophosphate.

The invention also provides methods for remineralizing teeth to reduce or eliminate dental caries and other dental disease. The methods of the invention are provided wherein a human patient simply chews the gums, candies or confectioneries of the invention, uses the toothpastes or dentifrices, or applies the gels of the invention to release calcium and phosphate ions into the mouth and onto teeth. In a preferred embodiment, the gum is chewed, candy or confectionery is chewed or used as a lozenge, the toothpaste or dentifrice is used, or the gel is applied, from about one to about five minutes, more preferably from about three to about ten minutes, and most preferably from about five to about fifteen or twenty minutes, to effect the release of calcium and phosphate ions into the mouth and in contact with teeth. In preferred embodiments, the gels of the invention are applied and allowed to remain in contact with teeth for about 8 hours or overnight.

A preferred use for the methods of this invention is for remineralizing a dental lesion in a human. Another preferred use for the methods of the invention is for remineralizing dental plaque in a human. Yet another preferred use for the methods of this invention is for reducing cariogenic challenge to human teeth. The methods of the invention are also preferably used for desensitizing hypersensitive human teeth, and for remineralizing open dentinal tubules and exposed dentine surfaces in human teeth.

Certain preferred embodiments of the gums, candies, confectioneries, toothpastes, dentifrices and gels of the invention, as well as useful methods for using such embodiments for treating and remineralizing teeth, are described in greater detail in the following sections of this application.

DETAILED DESCRIPTION OF THE INVENTION

It has been known for some time that hydroxyapatite materials have the basic properties of human bones and teeth. A considerable amount of research has been directed to the remineralization of incipient dental lesions, including plaque deposits, by deposition of hydroxyapatite, $Ca_5(PO_4)_3OH$, on such lesions, so that the hydroxyapatite is incorporated into the dental structure at the point of lesion.

Remineralization of tooth enamel has been carried out experimentally both in vivo and in vitro. These studies have concentrated on the remineralizing properties of saliva and synthetic solutions supersaturated with respect to hydroxyapatite. Chewing gums, candies and confectioneries, toothpastes, dentifrices and gels as provided herein are useful as vehicles for delivering hydroxyapatite-depositing calcium phosphate compositions to teeth in vivo. An advantage of these delivery vehicles is that calcium phosphates and compounds that release calcium and phosphate ions into the mouth are provided as simple mixtures in the chewing gum, candy, confectionery, toothpaste, dentifrice or gel, because delivery to teeth is effectively achieved simply by having a human use the delivery vehicle of the invention (e.g., by chewing the calcium phosphate-containing gums, candies and confectionaries and using the calcium phosphate-containing toothpastes, dentifrices and gels).

Compounds that release calcium and phosphate ion are selected from a number of commercially-available and other compounds that are recognized as food additives in other contexts. All such additives encompassed by the present invention are intended to be non-toxic. For the purpose of this invention, the term "non-toxic" is intended to conform with accepted and established definitions of safety, such as are described by the designation "generally accepted as safe" by the Food and Drug Administration. Also encompassed in this definition are those compounds that have been added to food for some time and which are recognized as safe under conditions of their intended use. The additives of the invention, including calcium and phosphate salts should be non-toxic enough for oral use at the intended levels on a regular basis, and stable for the desired shelf life.

Preferred calcium ion-releasing compounds are sparingly soluble calcium-containing salts of biologically-compatible acids and other basic calcium compounds, i.e., calcium compounds having a solubility greater than about 0.1% and less than about 10% under conditions of neutral pH. Sparingly soluble calcium compounds include but are not limited to the calcium salts of gluconate, glycerophosphate, lactate, and fumarate, $Ca(OH)_2$, CaO, monocalcium phosphate, dicalcium phosphate anhydrous, dicalcium phosphate dihydrate, α-tricalcium phosphate, octacalcium phosphate, tetracalcium phosphate, and combinations and mixtures thereof.

There are two major categories of gums useful as components of the instant invention: neutral pH gums and acidic pH gums. Acidic pH gums include most fruit flavored chewing gums and bubble gums. Neutral pH gums include all mint flavored gums and some other non-fruit flavored gums. It has been found that none of the calcium phosphate compounds tested (with the exception of monocalcium phosphate monohydrate) was capable of releasing calcium or phosphate ions unless the gum had an acidic pH and produced an acid pH in saliva (i.e., pH less than 7.0), as shown herein in Table III below. This new finding may explain why dicalcium phosphate dihydrate-containing mint-flavored (neutral pH) gums were previously reported to show only marginal anti-caries effects (see Finn and Jamison, 1967, ibid. and Richardson et al., 1972, ibid.). In contrast, monocalcium phosphate monohydrate (MCPM) was found to be capable of releasing calcium and phosphate ions into saliva from non-acidic gums (Table III). However, the acidity of MCPM produces a tart taste which may be incompatible with some gum flavors. In addition, MCPM produces an unpleasant after-taste if the gum contain more than 2 or 3% MCPM. Thus, the most useful calcium phosphate-containing gums are acidic pH gums, which represent only a minor portion of the gums being consumed.

However, neutral gums have surprising been found to be capable of releasing anticarious calcium phosphate agents under certain conditions, specifically, by adding separate calcium-containing and phosphate-containing compounds to the gum. Several non-toxic calcium compounds are sparingly soluble, and when used as chewing gum additives, allowed calcium ions to be released into saliva gradually and continuously (see Table IV). These compounds include the calcium salts of gluconic acid, lactic acid, fumaric acid, and glycerophosphoric acid. Unlike calcium phosphates, the solubilities of these calcium-containing compounds are essentially independent of pH, resulting in these additives being capable of performing well in both acid and neutral pH gums. In order to obtain significant calcium ion release, the calcium source should have a solubility that is greater than 0.5% at neutral pH; solubilities of 2% and above are preferred. Preferred calcium salts are sparingly soluble, that is, having a solubility of less than 10% at neutral pH. Calcium carbonate, and calcium citrate and calcium tartrate (the calcium salts of two commonly-used food acids) are too insoluble to produce effective release (see Table IV). On the other hand, highly soluble calcium-continuing compounds such as calcium acetate and calcium chloride are of limited usefulness because these compounds are incapable of sustained release of calcium ions from the chewing gums. (However, soluble calcium compounds may be useful with other delivery vehicles of this invention such as candies and confectioneries which take 5 minutes or longer to dissolve.)

The anticaries effects of calcium ion-releasing compounds of the invention are significantly augmented by adding a non-toxic phosphate salt as a second additive. Preferred phosphate salts include sodium phosphate (most preferably comprising an equimolar mixture of $Na_2HPO_4$ and $NaH_2PO_4$, to maintain pH at 7). Addition of sodium phosphate to the calcium ion-releasing additives of the invention results in the desired release of both calcium and phosphate ions in quantities capable of depositing calcium phosphate mineral (including hydroxyapatite) on the surface of teeth in vivo (see Table IV). In alternative embodiments, a sparingly-soluble calcium source can be admixed with a calcium phosphate salt, such as MCPM, which serves as a source for both calcium and phosphate ions.

Candies and confectioneries of the invention comprise preferably sweeteners such as sorbitol, mannitol, aspartame and saccharine. Sugar (specifically sucrose, fructose, glucose, and combinations thereof) containing candies and confectionaries are also provided by the invention. Flavorings, such as citrus and other flavorings, that are naturally acidic are used to provide an advantageous acidic environment as discussed above. In addition, calcium compounds having substantially higher solubility than those calcium compounds useful in the gums and dentifrices of the invention can be used in the candies and confectioneries as provided herein; non-limiting examples of such calcium compounds are calcium chloride and calcium acetate. Preferred candies of the invention are non-chewable hard candies. Preferably, particles of the calcium and phosphate compounds comprising the candies and confectioneries of the invention are uniformly distributed throughout the candy or confectionery. In preferred embodiments, the candies and confectioneries of the invention are formulated wherein calcium and phosphate ions are released from the candies and confectioneries as they dissolve. It will be understood that the release rate of the calcium and phosphate ions depends on the concentration and distribution of these ions in the candies and confectioneries and on the rate of dissolution of the candies and confectioneries, which in turn is dependent on the surface area of the candy or confectionery and its composition. In these formulations, the solubilities of the calcium and phosphate-containing compounds contribute relatively less to the release rates of calcium and phosphate ions than does the candy or confectionary dissolution rate. Calcium and phosphate ion release kinetics can be formulated accordingly by those of skill in the art based on these parameters.

Remineralizing gels of the invention comprise a non-toxic gelling compound as are conventionally used in foods, including but not limited to agar, geletine, carboxymethyl cellulose, chitin, gum acacia, gum arabic, gum xanthum, hydroxyethyl cellulose and hydroxypropyl methylcellulose. The gels of the invention are formulated to have a neutral pH to avoid irritation of oral tissues upon prolonged exposure. Each gel also comprises sufficient water or other aqueous solution to produce the desired consistency, as well as high molecular weight crystal growth inhibitors, and flavoring and coloring agents. High molecular weight crystal growth inhibiting agents include the gelling agents themselves, as described above, and also phosphoproteins (such as are disclosed in Termine & Conn, 1976, *Calcif. Tiss. Res.* 2: 149–157), polycarboxylates (such as are disclosed in Howie-Meyers et al., 1995, in *Mineral Scale Formation and Inhibition*, Amjad, ed., Plenum Press: New York, Ch. 15, pp. 169–182), and polyphosphorylated polyvinyl alcohol (as are described in Shimabayashi et al., 1995, in *Mineral Scale Formation and Inhibition*, Amjad, ed., Plenum Press: New York, Ch. 14, pp. 157–168). Such gels also comprises a sparingly-soluble calcium salt or a phosphate salt as described above for the gums of the invention.

Calcium phosphate-containing gels of the invention are preferably provided as a dry powder comprising the calcium phosphate compound and, optionally, dry flavorings, sweeteners, gelling agents, and other components are described above. In these embodiments, the gel is reconstituted by adding water or other liquid comprising advantageous additives (such as colorings, flavorings, sweeteners, gelling agents, and the like).

Dentifrices and toothpastes of the invention comprise conventional components of dentifrices and toothpastes, including but not limited to sweeteners such as sorbitol or saccharine, abrasives such as hydrated silica, foaming agents such as sodium lauryl sulfate, binders such as various forms of cellulose or gums, lubricants such as glycerin, pigment whiteners such as titanium oxide, food coloring and water.

As with the gels of the invention, the dentifrices and toothpastes of the invention are advantageously provided as a dry powder comprising the calcium phosphate compound and, optionally, dry flavorings, sweeteners, gelling agents, and other components are described above. In these embodiments, the gel is reconstituted by adding water or other liquid comprising advantageous additives (such as colorings, flavorings, sweeteners, gelling agents, and the like).

An additive of particular significance in dental applications is fluoride containing compounds. In toothpaste and gel embodiments of this invention, fluoride salts such as NaF, $CaF_2$, $SnF_2$, $Na_2PO_3F$ or $Na_2SiF_6$ are added in sufficient quantity they increase the rate of formation of HA and fluorapatite. Preferably, embodiments of the invention will have a fluoride content of about 200 to 2200 ppm. The total amount of fluoride released during use of the toothpastes gels of this invention is 0.05 to 10 mg.

Using the chewing gums of the invention, sustained release of calcium and phosphate ions from the gums, candies and other delivery vehicles of the invention should be maintained for at least about 3–5 minutes and preferably, at least about 3–10 minutes and most preferably, at least about 3–15 minutes.

The following Examples are intended to further illustrate certain preferred embodiments of the invention and are not limiting in nature.

EXAMPLES

Preparation of calcium phosphate-containing gums

Calcium phosphate-containing gums were prepared as follows. Calcium lactate, calcium gluconate, calcium glycerophosphate, monocalcium phosphate monobasic, disodium hydrogen phosphate, and sodium dihydrogen phosphate were all obtained commercially as food grade chemicals. α-tricalcium phosphate (α-TCP) was prepared by heating a mixture containing 2 moles of commercially-available DCPA and 1 mole of commercially available calcium carbonate ($CaCO_3$) to 1200° C. for 6 h. Gums used were LifeSaver® peppermint gum (as a neutral pH gum) or LifeSavers® grape flavored bubble gum (as an acidic pH gum). Experimental gums were prepared by uniformly dispersing the calcium phosphate additive into the control gums.

Release of calcium and phosphate ions from the gum into saliva

The ability of calcium phosphate-containing chewing gums of the invention to release calcium and phosphate ions into the mouth upon chewing by a subject was determined as follows. Three human subjects with normal salivary flow ($\geq 0.2$ mL saliva per minute) chewed gums with or without various formulations of calcium phosphate for between 0–16 minutes. Saliva samples were collected at intervals of either 0–2 minutes or 14–16 minutes. Calcium ion concentration in the saliva samples were determined using a calcium electrode (Orion; see Vogel et al., 1987, *J. Dent. Res.* 66: 1691–1697). Phosphate ion concentration in saliva were determined by spectrophotometry (Vogel et al., *ibid.*).

The results of these studies are shown in Table I below. The data in Table I show the effect on salivary calcium ion concentration in saliva released after chewing an acidic pH gum containing 1 to 5 wt % A-TCP was chewed. Calcium ion release from the 5% A-TCP gum was statistically equivalent to that of the 5% (DCPA/TTCP) gum.

TABLE I

| Release of Ca into Saliva from Acid pH Gums Containing Various Calcium Phosphate Additives | | |
|---|---|---|
| | Calcium Concentration#, mmol/L | |
| Additive | 0–2 min. | 14–16 min |
| control | 0.41 ± 0.27 | 0.80 ± 0.30 |
| 5% (TTCP/DCPA) | 10.08 ± 1.72 | 1.29 ± 0.10 |
| 5% α-TCP | 9.04 ± 2.03 | 1.82 ± 0.59 |
| 2.5% α-TCP | 4.27 ± 0.72 | 1.81 ± 0.86 |
| 1% α-TCP | 2.71 ± 0.01 | 1.02 ± 0.05 | mean ± s.d (n = 3)

Effects of gum chewing on plaque composition

The ability of calcium phosphate-containing chewing gums of the invention to remineralize plaque upon chewing by a subject was determined as follows. Twelve human subjects with normal salivary flow chewed gums with or without various formulations of calcium phosphate. In these experiments, plaque was allowed to accumulate for 48 h prior to each experiment. Baseline samples of plaque were collected prior to the beginning of each experiment, and then subjects rinsed the oral cavity with a 10% sucrose solution for about 1 min. Subjects then chewed control or experimental gums for between 0–15 minutes. Two pooled plaque samples from upper and lower molars of each subject were collected 7 and 15 min after gum chewing began, with 1 min saliva samples collected just before each plaque sample. For each sample, plaque pH was determined using microelectrodes (glass pH electrode; Vogel et al., 1990, *J. Dent. Res.* 69: 1316–1323). In addition, plaque fluid was separated from plaque solids by centrifugation and acidified with 0.1 M perchloric acid to prevent precipitation of calcium phosphate (as the result of increased calcium phosphate levels in saliva and removal of dissolved carbonate anion as carbon dioxide from saliva after sample collection). Free calcium ion concentration in the saliva samples were determined using a calcium electrode as described above. Total calcium and phosphate ion concentration in saliva were determined by spectrophotometry (as described in Vogel et al., *ibid.*). Data on salivary and plaque pH, and calcium and phosphate ion concentrations were used to calculate the degree of saturation with respect to tooth mineral in plaque.

The results from these experiments are shown in Table II. The data in Table II show that chewing gum containing 2.5% α-TCP produced significant increases in the calcium and phosphate ion concentrations in plaque. These increases prevented a decrease in mineral saturation in plaque after sucrose intake and completely eradicated the acidic challenge produced by sucrose. In contrast, the subject group that used the control gum experienced a decreased plaque mineral saturation level after the sucrose rinse that was indicative of increased caries risk.

The results of experiments with neutral pH gums are shown in Table III. The data in Table III show that calcium and phosphate ions are not efficiently released from a neutral pH gum (LifeSavers® Peppermint gum). In fact, none of the calcium phosphate compounds tested (with the exception of MCPM) was capable of releasing calcium or phosphate ions unless the gum has an acidic pH and produces an acid pH in saliva (i.e., pH less than 7.0; compare the data in Table I with the data in Table III).

TABLE II

Release of $Ca^{++}$ Ions Into Saliva from pH Neutral Gums Containing Calcium Phosphate Additives

| Additive | Calcium Concentration[1], mmol/L | |
|---|---|---|
| | 0–2 min. | 14–16 min |
| Control | 1.11 ± 0.11 | 0.90 ± 0.07 |
| 5% (TTCP/DCPA) | 0.82 ± 0.03 | 0.82 ± 0.02 |
| 5% α-TCP | 0.72 ± 0.03 | 0.77 ± 0.03 |
| 5% TTCP | 1.03 ± 0.14 | 1.05 ± 0.22 |
| 2% MCPM | 3.74 ± 0.68 | 1.15 ± 0.20 |
| 5% MCPM | 6.56 ± 0.84 | 0.92 ± 0.23 |

[1]mean ± s.d. (n = 3)

In other experiments, neutral gums were used to release anticarious calcium phosphate agents under certain conditions. This was achieved by adding separate calcium-containing and phosphate-containing compounds to the gum. Calcium-containing compounds used as separate calcium-containing additives were the calcium salts of gluconic acid, lactic acid, fumaric acid, and glycerophosphoric acid. Results using these compounds are shown in Table IV. In these experiments it was found that the solubilities of these calcium-containing compounds are essentially independent of pH (in contrast to calcium phosphate compounds, which require acidic pH). Calcium carbonate and the calcium salts of two commonly used food acids, citric acid and tartaric acid, were too insoluble to produce effective release

TABLE II

Plaque Composition After A Sucrose Rinse and Chewing Acidic pH Gums

| Time (min) | pH | | [Ca]$_F$ | | [Ca]$_T$ | | [P]$_T$ | | pIAP | |
|---|---|---|---|---|---|---|---|---|---|---|
| | Ctrl[1] | Exp[2] | Ctrl | Exp | Ctrl | Exp | Ctrl | Exp | Ctrl | Exp |
| −1 | 7.08[3] | 7.07 | 0.77 | 0.83 | 1.87 | 1.89 | 13.1 | 12.5 | 48.5 | 49.2 |
| | (.45)[3] | (.33) | (.27) | (.48) | (.50) | (.78) | (2.6) | (1.3) | (1.4) | (1.6) |
| −1 to 0 | | | | SUCROSE CHALLENGE | | | | | | |
| 0 to 15 | | | | GUM CHEWING | | | | | | |
| 7 | 6.15 | 6.50 | 1.42 | <3.58[4] | 2.69 | <5.82 | 8.88 | <11.1 | 52.7 | >48.8 |
| | (.42) | (.48) | (.50) | (1.9) | (.78) | (2.0) | (1.2) | (3.0) | (2.3) | (1.9) |
| 15 | 5.58 | 6.31 | 1.33 | <2.51 | 2.23 | <3.96 | 8.69 | 9.70 | 50.4 | >47.8 |
| | (.50) | (1.9) | (.34) | (1.37) | (.70) | (1.53) | (1.64) | (1.84) | (2.5) | (1.0) |

[1]Control Gum was LifeSavers Grape Flavored Bubble Gum.
[2]Experimental Gum was the 2.5% α-TCP added to the control gum.
[3]mean (std dev); n = 12 to 14
[4]Means of the control and experimental groups are significantly different (p < 0.05).
[Ca]$_F$ = free Ca concentration (mmol/L) measured by Ca electrode; [Ca]$_T$ and [P]$_T$ = total Ca and P concentrations measured by spectrophotometric methods;
pIAP = −log(IAP) where IAP is ion activity product of hydroxyapatite.

Effect of Gum Composition on Calcium and Phosphate ion Release

Two types of gums were tested as components of the invention: neutral pH and acidic pH gums. An example of an acidic pH gum tested was LifeSavers® Grape bubble gum, as disclosed above in Table I. A neutral pH gum tested was LifeSavers® Peppermint gum, in experiments performed as described above to produce the data comprising Table I.

(Table IV). The anticaries effects derived from the calcium compounds were significantly augmented by adding an equimolar mixture of $Na_2HPO_4$ and $NaH_2PO_4$ (to maintain pH at 7). This caused a significant release of phosphate ions into saliva. The data further showed that the combination of a calcium source (e.g., calcium glycerophosphate) and a phosphate source (e.g., sodium phosphate) in a gum resulted in the desired release of both calcium and phosphate ions. It was also found that a sparingly-soluble calcium source (such as calcium glycerophosphate) could be used with MCPM (which served as a source for both calcium and phosphate ions).

TABLE IV

Release of Calcium and Phosphate Ions Into Saliva from pH Neutral Gums Containing Separate Calcium and Phosphate Additives

| Additive | | Concentration[1], mmol/L | |
|---|---|---|---|
| | | 0–2 min | 14–16 min |
| Control | [Ca] | 1.11 ± 0.11 | 0.90 ± 0.07 |
| *5% Ca lactate | [Ca] | 10.3 ± 2.20 | 2.48 ± 0.20 |
| 5% Cagluconate | [Ca] | 4.85 ± 1.32 | 1.87 ± 0.27 |
| 5% Ca citrate | [Ca] | 1.20 ± 0.12 | 1.30 ± 0.13 |
| 5% Ca glycerophosphate | [Ca] | 8.84 ± 1.45 | 2.14 ± 0.71 |
| | [P] | 3.59 ± 1.33 | 3.51 ± 0.73 |
| 3% Ca glycerophos- | [Ca] | 5.80 ± 0.54 | 1.21 ± 0.09 |
| phate + 2% MCPM | [P] | 12.8 ± 1.70 | 6.63 ± 1.70 |
| 2% Na phosphate | [Ca] | 0.55 ± 0.07 | 0.76 ± 0.14 |
| | [P] | 20.3 ± 0.26 | 4.15 ± 0.70 |
| 5% Cacarbonate | [Ca] | 0.80 ± 0.00 | 0.93 ± 0.07 |

[1]mean ± s.d. (n = 3)

Preparation of calcium phosphate-containing remineralizing toothpastes

One embodiment of the remineralizing toothpastes of the invention comprise a calcium-containing component and a phosphate-containing component, stored in separate containers to prevent premature development of hydroxyapatite in the presence of the wet components of the toothpaste. In a first example, a calcium phosphate-containing toothpaste is prepared as described in Table V. In this example, the calcium source is calcium glycerophosphate and the phosphate cource is monohydrogenphosphate heptahydrate and sodium dihydrogen phosphate. The phosphate-containing component also advantageously contains sodium fluoride as a fluoride source. A second example of a calcium phosphate-containing toothpaste is shown in Table VI. In this example, the calcium source is calcium gluconate and the phosphate source is monocalcium phosphate monohydrate. The phosphate-containing component also advantageously contains sodium monofluorophosphate as a fluoride source instead of sodium fluoride, since the latter fluoride source will react with monocalcium phosphate monohydrate to form calcium fluoride and fluoroapatite (thus preventing the release of either phosphate or fluoride in the toothpaste during application). In both examples, the toothpastes are forumulated so that the calcium source component and the phosphate source component are used in equal amounts (by weight) during application, using established packaging means and other methods known in the dental arts.

TABLE V

Reminералzing Toothpaste Example 1

| Component | Paste A | Paste B |
|---|---|---|
| calcium glycerophosphate | 4.2 g | 0 |
| sodium monohydrogen phosphate heptahydrate | 0 | 2.68 g |
| sodium dihydrogen phosphate dihydrate | 0 | 1.56 g |
| sodium fluoride | 0 | 0.48 g |
| sorbitol (70% solution) | 15 g | 15 g |
| silica | 35 g | 35 g |
| glycerine | 15 g | 15 g |
| sodium carboxymethyl cellulose | 1 g | 1 g |

TABLE V-continued

Reminералzing Toothpaste Example 1

| Component | Paste A | Paste B |
|---|---|---|
| sodium n-lauryl sarcosinate | 1 g | 1 g |
| water, coloring, flavoring | q.s. to 100 g | q.s. to 100 g |

TABLE VI

Reminералzing Toothpaste Example 2

| Component | Paste A | Paste B |
|---|---|---|
| calcium gluconate | 8.96 g | 0 |
| monocalcium phosphate monohydrate | 0 | 2.52 g |
| sodium monofluorophosphate | 0 | 1.67 g |
| sorbitol (70% solution) | 15 g | 15 g |
| silica | 35 g | 35 g |
| glycerine | 15 g | 15 g |
| sodium carboxymethyl cellulose | 1 g | 1 g |
| sodium n-lauryl sarcosinate | 1 g | 1 g |
| water, coloring, flavoring | q.s. to 100 g | q.s. to 100 g |

Another embodiment of the remineralizing toothpastes of the present invention comprises a dry powder containing a calcium phosphate source. Preferred calcium phosphate compositions are tetracalcium phosphate, α-tricalcium phosphate and monocalcium phosphate. Upon use the powder can be mixed with a liquid, i.e., water, to form a paste. The paste is then applied to the teeth.

Preparation of calcium phosphate-containing gels

All remineralizing gels comprise a calcium-containing component and a phosphate-containing component, stored in separate containers to prevent premature development of hydroxyapatite in the presence of the wet components of the gel. In a first example, the formulation of which is shown in Table VII, these components comprise a liquid component and a dry (powder) component. In this embodiment, the liquid is combined with the powder immediately prior to use to obtain a smooth gel, which is then applied to the areas in which remineralization is desired (including, for example, sensitive root surfaces and caries lesions on the chewing surfaces of teeth). In the practice of this aspect of the invention, it is anticipated that an amount of about 10 g of the gel described herein will be advantageously applied for remineralizing purposes, and the example set out in Table VII is formulated therefore.

TABLE VII

Remineralizing Gel Example 1

| Components | Dry Powder | Liquid |
|---|---|---|
| α-tricalcium phosphate | 0.8 g | 0 |
| sodium carboxymethyl cellulose | 0.35 g | 0 |
| sodium fluoride | 0.024 g | 0 |
| sorbitol (70% solution) | 0 | 1.5 g |
| water | 0 | 7.326 g |

In a second example, the formulation of which is shown in Table VII, the formulation comprises an equal amount of two gels, one comprising a calcium source and the other comprising a phosphate source, which are mixed immediately prior to use to produce a homogeneous gel.

TABLE VIII

Remineralizing Gel Example 2

| Component | Gel 1 | Gel 2 |
| --- | --- | --- |
| calcium glycerophosphate | 8.4 g | 0 |
| sodium monohydrogen phosphate heptahydrate | 0 | 5.36 g |
| sodium dihydrogen phosphate dihydrate | 0 | 3.12 g |
| sodium fluoride | 0 | 0.95 g |
| sorbitol (70% solution) | 15 g | 15 g |
| sodium carboxymethyl cellulose | 6 g | 6 g |
| water, flavoring, coloring | q.s. to 100 g | q.s. to 100 g |

Preparation of calcium phosphate-containing candies

Both sugar-free candies (Table IX) and sugar-containing candies (Table X) are described. In this aspect of the invention, calcium and phosphate sources can be combined in the same phase without concern of premature hydroxyapatite-producing reactions between the two compounds, since there is essentially no free water in such candies.

TABLE IX

Remineralizing Sugar-Free Candy Example

| Component | Amount |
| --- | --- |
| calcium glycerophosphate | 8.4 g |
| sodium monohydrogen phosphate heptahydrate | 5.36 g |
| sodium dihydrogen phosphate dihydrate | 3.12 g |
| sorbitol, flavoring, coloring | q.s. to 100 g |

TABLE X

Remineralizing Candy Example

| Component | Amount |
| --- | --- |
| α-tricalcium phosphate | 8 g |
| sugar, corn syrup, flavoring, coloring | q.s. to 100 g |

It should be understood that the foregoing disclosure emphasizes certain specific embodiments of the invention and that all modifications or alternatives equivalent thereto are within the spirit and scope of the invention as set forth herein.

We claim:

1. A remineralizing composition in the form of a gel, toothpaste or dentifrice comprising, in combination:
a toothpaste or dentifrice mixed with a sparingly soluble calcium phosphate salt in dry particle form, said salt capable of sustained release of both calcium and phosphate ions into saliva upon exposure of the particle thereto and providing a hydroxyapatite remineralization, said salt selected from the group consisting essentially of tetracalcium phosphate, tricalcium phosphate and monocalcium phosphate.

2. A gel, toothpaste or dentifrice remineralization system comprising, in combination:
a sparingly soluble calcium compound and a separate phosphate salt, said compound and said salt each separately combined with a separate gel, toothpaste or dentifrice, said compound and said salt capable, respectively, of sustained release of calcium and phosphorous ions in the presence of water for at least about 1–5 minutes thereby forming hydroxyapatite as an end product when said gel, toothpaste or dentifrice containing, respectively, said salt and said compound are mixed in the presence of water.

3. The remineralizing gel, toothpaste or dentifrice composition of claim 1, wherein the calcium phosphate salt comprises from 0.5 to 10 weight percent.

4. The remineralizing gel, toothpaste or dentifrice composition of claim 1, wherein the calcium phosphate salt comprises from 1 to 5 weight percent.

5. The remineralizing gel, toothpaste or dentifrice composition of claim 1, wherein the calcium phosphate salt comprising the remineralizing gel has a particle size of less than 50 $\mu$m.

6. The remineralizing gel, toothpaste or dentifrice composition of claim 1, wherein the calcium phosphate salt comprising the remineralizing gel has a particle size of 1 to 20 $\mu$m.

7. A method of remineralizing a dental lesion in a human, the method comprising the step of having the human apply a remineralizing gel, toothpaste or dentifrice composition according to claim 1.

8. A method of remineralizing dental plaque in a human, the method comprising the step of having the human apply a remineralizing gel, toothpaste or dentifrice composition according to claim 1.

9. A method of reducing cariogenic challenge to human teeth, the method comprising the step of having the human apply a remineralizing gel, toothpaste or dentifrice composition according to claim 1.

10. A method of desensitizing hypersensitive human teeth, the method comprising the step of having the human apply a remineralizing gel, toothpaste or dentifrice composition according to claim 1.

11. The composition or system of claim 1 or 2 further including a fluoride compound.

12. The composition or system of claim 11 wherein said fluoride compound comprises NaF, $CaF_2$, $SuF_2$ $Na_2Po_3F$, $NaSiF_6$ providing a fluoride content in the range of about 200 to 2200 ppm.

13. The system of claim 2 wherein said salt and compound are capable of sustained release in the range of at least 3–15 minutes.

14. The system of claim 2 further including a macro molecular crystal growth inhibitor.

15. The system of claim 14 wherein said growth inhibitor comprises cellulose compounds.

16. The system of claim 15 wherein said growth inhibitor comprises carboxymethyl cellulose or sodium and potassium pyrophosphate.

17. A remineralizing gel, toothpaste or dentifrice system according to claim 2, wherein the sparingly-soluble calcium compound is selected from the group consisting of the calcium salts of glycerophosphate, lactate, gluconate, and fumarate.

18. A remineralizing gel, toothpaste or dentifrice system according to claim 2, wherein the sparingly-soluble calcium compound comprises from 0.5 to 10 weight percent.

19. The remineralizing gel, toothpaste or dentifrice system of claim 2, wherein the sparingly-soluble calcium compound comprises from 1 to 5 weight percent.

20. The remineralizing gel, toothpaste or dentifrice system of claim 2, wherein the sparingly-soluble calcium compound comprising the remineralizing gel, toothpaste or dentifrice has a particle size of less than 50 $\mu$m.

21. The remineralizing gel, toothpaste or dentifrice system of claim 2, wherein the sparingly-soluble calcium compound comprising the remineralizing gel has a particle size of 1 to 20 μm.

22. The remineralizing gel, toothpaste or dentifrice system of claim 2, wherein the phosphate salt is selected from the group consisting of $Na_2HPO_4$, $NaH_2PO_4$, and $Ca(H_2PO_4)_2 \cdot H_2O$.

23. The remineralizing gel, toothpaste or dentifrice system of claim 2, wherein the phosphate salt comprises 0.5 to 10 weight percent.

24. The reminerlizing gel, toothpaste or dentifrice system of claim 2, wherein the phosphate salt comprising the remineralizing gel, toothpaste or dentifrice has a particle size of less than 50 μm.

25. The remineralizing gel, toothpaste or dentifrice system of claim 2, wherein the phosphate salt comprising the remineralizing gel, toothpaste or dentifrice has a particle size of 1 to 20 μm.

26. A method of remineralizing a dental lesion in a human, the method comprising the step of having the human apply a remineralizing gel, toothpaste or dentifrice system according to claim 2.

27. A method of remineralizing dental plaque in a human, the method comprising the step of having the human apply a remineralizing gel, toothpaste or dentifrice system according to claim 2.

28. A method of reducing cariogenic challenge to human teeth, the method comprising the step of having the human apply a remineralizing gel, toothpaste or dentifrice system according to claim 2.

29. A method of desensitizing hypersensitive human teeth, the method comprising the step of having the human apply a remineralizing gel, toothpaste or dentifrice system according to claim 2.

* * * * *

UNITED STATES PATENT AND TRADEMARK OFFICE
CERTIFICATE OF CORRECTION

PATENT NO.        : 5,993,786
APPLICATION NO.   : 09/088869
DATED             : November 30, 1999
INVENTOR(S)       : Laurence C. Chow et al.

Page 1 of 1

It is certified that error appears in the above-identified patent and that said Letters Patent is hereby corrected as shown below:

In the Specification

The following should replace the paragraph in Column 1, at Lines 8 - 12:
STATEMENT OF FEDERALLY SPONSORED RESEARCH
This invention was made with government support under grants DE005354 and DE010840 awarded by the National Institutes of Health. The government has certain rights in the invention.

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*